United States Patent [19]

Rapoport et al.

[11] Patent Number: 4,655,213

[45] Date of Patent: Apr. 7, 1987

[54] METHOD AND APPARATUS FOR THE TREATMENT OF OBSTRUCTIVE SLEEP APNEA

[75] Inventors: David M. Rapoport; I. Barry Sorkin, both of New York, N.Y.

[73] Assignee: New York University, N.Y.

[21] Appl. No.: 539,723

[22] Filed: Oct. 6, 1983

[51] Int. Cl.⁴ ............................................. A61M 16/00
[52] U.S. Cl. ........................... 128/205.25; 128/207.12; 128/207.13
[58] Field of Search ................... 128/203.28, 203.29, 128/204.18, 204.21, 204.25, 204.26, 205.11, 205.12, 205.13, 205.17, 205.18, 205.19, 205.24, 205.25, 207.12, 207.13, 207.18, 911

[56] References Cited

U.S. PATENT DOCUMENTS

| | | | |
|---|---|---|---|
| 7,476 | 7/1850 | Lane | 128/205.17 |
| 1,109,318 | 9/1914 | Browne et al. | 128/203.29 |
| 1,162,416 | 11/1915 | Teter | 128/207.12 |
| 1,263,595 | 4/1918 | Nondstrom . | |
| 1,632,449 | 6/1927 | McKesson | 128/207.13 |
| 2,016,212 | 10/1935 | O'Connell | 128/207.13 |
| 2,122,897 | 7/1938 | Straw | 128/204.18 |
| 2,241,535 | 5/1941 | Boothby et al. | 128/205.17 |
| 2,300,273 | 10/1942 | Connell | 128/205.17 |
| 2,376,971 | 5/1945 | Kleit | 128/207.13 |
| 2,408,136 | 9/1946 | Fox | 128/204.25 |
| 3,357,428 | 12/1967 | Carlson . | |
| 3,362,404 | 1/1968 | Beasley . | |
| 3,584,621 | 6/1971 | Bird et al. . | |
| 3,799,164 | 3/1974 | Rollins . | |
| 3,889,671 | 6/1975 | Baker . | |
| 4,077,404 | 3/1978 | Elam | 128/205.24 |
| 4,151,843 | 5/1979 | Brekke et al. | 128/207.18 |
| 4,249,527 | 2/1981 | Ko et al. | 128/911 |
| 4,266,540 | 5/1981 | Panzik et al. . | |
| 4,334,533 | 6/1982 | Henkin | 128/914 |
| 4,354,488 | 10/1982 | Bartos . | |
| 4,462,398 | 7/1984 | Durkan et al. | 128/204.24 |

FOREIGN PATENT DOCUMENTS

| | | | |
|---|---|---|---|
| 223220 | 6/1910 | Fed. Rep. of Germany | 128/207.18 |
| WO82/03548 | 10/1982 | PCT Int'l Appl. | 128/207.13 |
| 684788 | 12/1952 | United Kingdom | 128/207.13 |

OTHER PUBLICATIONS

Sullivan et al., "Reversal of Obstructive Sleep Apnea by Continuous Positive Airway Pressure Applied Through the Nares", Lancet, 1981, 1:862-865.
Rapoport et al., "Reversal of the Pickwickian Syndrome by Long-Term Use of Nocturnal Nasal-Airway Pressure", 10/7/82, New England Journal of Medicine, 307:931-933.

Primary Examiner—Henry J. Recla
Attorney, Agent, or Firm—Rosen, Dainow & Jacobs

[57] ABSTRACT

A nose mask assembly for the treatment of obstructive sleep apnea which is comprised of a nose mask adapted to be sealed over the nose of a patient, an inlet for supplying a continuous positive pressure of air to the mask and a threshold valve to release air from the mask.

1 Claim, 2 Drawing Figures

METHOD AND APPARATUS FOR THE TREATMENT OF OBSTRUCTIVE SLEEP APNEA

This invention relates to a method and mask for the treatment of obstructive sleep apnea, and is particularly directed to such a method and apparatus wherein a positive pressure is applied to the nares of a patient by means of a nose mask.

The syndrome of obstructive sleep apnea is a common disorder, especially in middle-aged obese males. The problem arises in sleep-induced occlusion of the oropharyngeal airway, resulting in multiple apneic occurrences during sleep. As a consequence, there is a severe interruption of sleep in the patient, and, as the disease progresses over periods of time, greater degrees of asphyxia occur. The duration of apnea may exceed two minutes, with the arterial hemoglobin oxygen saturation falling below 50 percent. The patient may be entirely unaware of the occurence of these frequent obstructions to breathing. The symptoms are generally excessive day-time sleepiness, and snoring. The nocturnal asphyxia may eventually lead to a number of further problems, such as cardiac arrhythmia, pulmonary hypertension and right heart failure, systemic hypertension, severe morning headache, intellectual and personality changes and polycythemia.

One method of treatment for the disease is a tracheostomy, which is left open at night. Medical and psychosocial problems frequently interfere with the acceptance of tracheostomy, both by the patient and the physician, and this solution has generally been employed only in severe cases. Patients have frequently choosen to accept the discomfort associated with the disease rather than have a tracheostomy.

It has been suggested that continuous positive airway pressure (CPAP) be applied to the patient, during periods of sleep, by way of the nose ("Reversal of obstructive sleep apnea by continuous positive airway pressure applied through the nares", Colin Sullivan et al. The Lancet, Apr. 18, 1981, pages 862–865). Sullivan et al. suggests the application of low levels of pressure, in the range of 4.5 to 10 centimeters H2O, and reported that this procedure completely prevented upper airway occlusion during sleep, allowing the patients to have entire nights of uninterrupted sleep. The continuous positive airway pressure applied in this manner may provide a pneumatic splint for the nasopharyngal airway.

In the arrangement provided by Sullivan et al., two soft plastic tubes were shaped to fix snuggly in each naris. The other ends of these tubes were inserted into a lightweight wide-bore tube, the arrangement being strapped to the patients face. A medical grade silicone rubber was then run over the nose and nares to provide a seal. Continuous positive pressure was produced by connecting one end of the wide-bored tube to an air compressor motor with variable speed control. The other end of the wide-bore tube was led away from the patient and narrowed, to provide a mechanical resistance. The resistance of the circuit was choosen so that a high bias flow (20–40 liters per minute) was sustained for the range of pressures required at the nose.

While the CPAP procedure as reported by Sullivan et al. may provide temporary relief, i.e., patients with severe disease may satisfactorily employ the technique for several nights, the required cumbersome physical equipment renders this solution satisfactory only for in-hospital management of patients, hence being practical only for severely affected patients. The uncomfortableness of the arrangement is not conducive to continual use by patients in the home environment.

While various masks have been employed in the past for respiration purposes, conventional respiration masks also cover the mouth, and are designed primarily for temporary use or for use with persons who do not require comfort. Such masks may be employed for anesthesia or resuscitation. A full face mask of this type is not satisfactory for patients with obstructive sleep apnea. The treatment relies on the difference in pressure between nose and mouth to open the airway. Furthermore, leaving the mouth uncovered allows the patient to breathe normally while awake and in case of failure of the air compressor or valve. Comfort is critical since a lack of willingness of a patient to continually employ a mask during sleeping hours defeats the purpose of the treatment.

In further masks, such as provided, for example, for dental applications, the nose masks have face seals such that they can not be pressurized. Application of CPAP absolutely requires the maintenance of pressure.

The present invention is therefore directed to the provision of a method and apparatus for the application of CPAP by means of a comfortable nose mask, for the treatment of apnea, whereby patients exhibit no discomfort from the use of the mask.

Briefly stated, in accordance with the invention, the above object is achieved by provision of a nose mask incorporating a threshold valve, wherein the air pressure continually applied to the mask is continually released from the mask, by means of a valve, at such a pressure that normally some pressurized air always escapes from the mask by way of the valve. This feature serves to maintain the air pressure at the nose, in order to maintain the nasopharyngel airway open, as well as to provide a continuous flow of fresh air to the mask so that the patient may exhale through the mask, with the exhaled air being immediately exhausted through the valve.

Since the threshold valve employed in the mask in accordance with the invention may be a very simple device, it may be readily miniaturized, so that the mask assembly may be very small and lightweight, thereby being comfortable to wear. The air supply tube may be a single small very flexible tube, enabling the patient to move around at night without difficultly. The ease of movement is further enhanced by the provision of a swivel joint at the junction of the valve and mask.

In order that the invention will be more clearly understood, it will now be disclosed in greater detail, with reference to the accompanying drawings, wherein.

Figure 1:
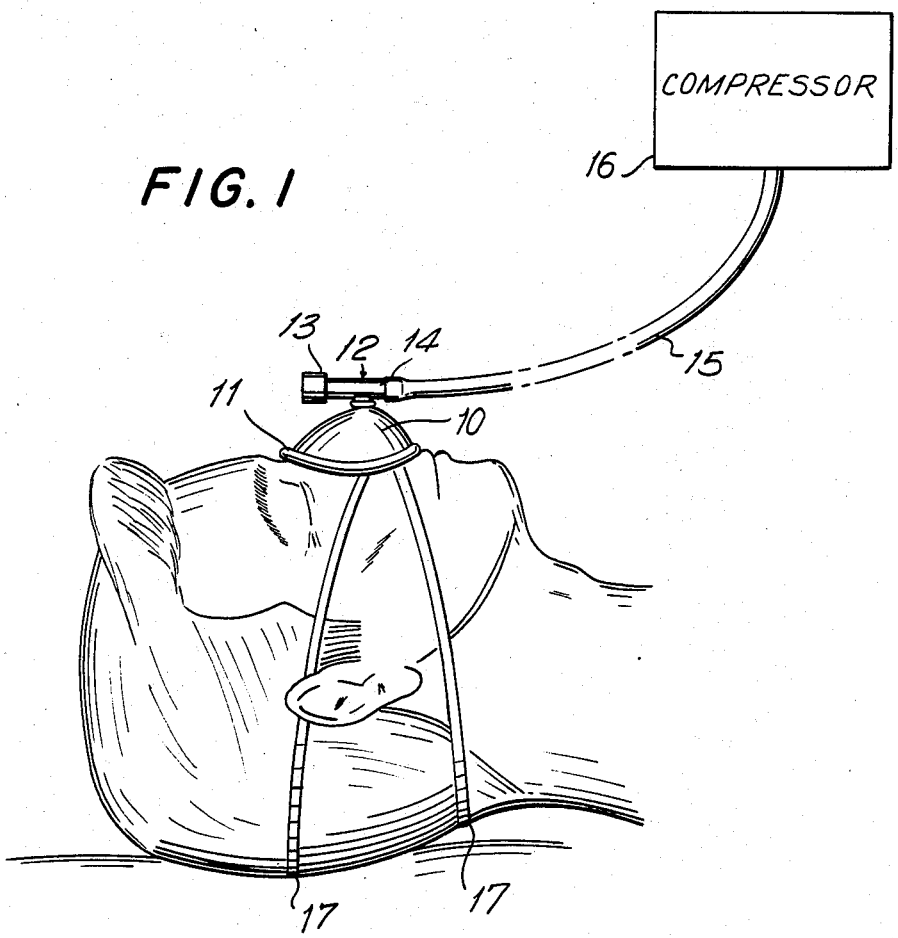
FIG. 1 is a view of a patient wearing a mask in accordance with the invention.

Referring now to FIG. 1, a generally cup-shaped nose piece 10 is provided with a rim 11 for lightly sealing the mask to the face. The rim 11 is preferably an air cuff, i.e., a flexible donut-shaped member, fitted to the edge of the mask and containing a pressurized gas. It is of course apparent that other sealing rims may be employed for the mask.

The nose mask is further provided with a valve assembly 12 including a threshold valve 13 for continually relieving air within the mask at a pressure such that the valve normally not be closed in use. In addition, the assembly 12 has an extension 14 adapted to be connected to an air supply tube 15, the tube 15 receiving compressed air from a conventional compressor 16.

In order to hold the nose mask on the face of the patient, lightweight flexible straps 17 may be connected to the mask to extend around the head of the patient.

Figure 2:
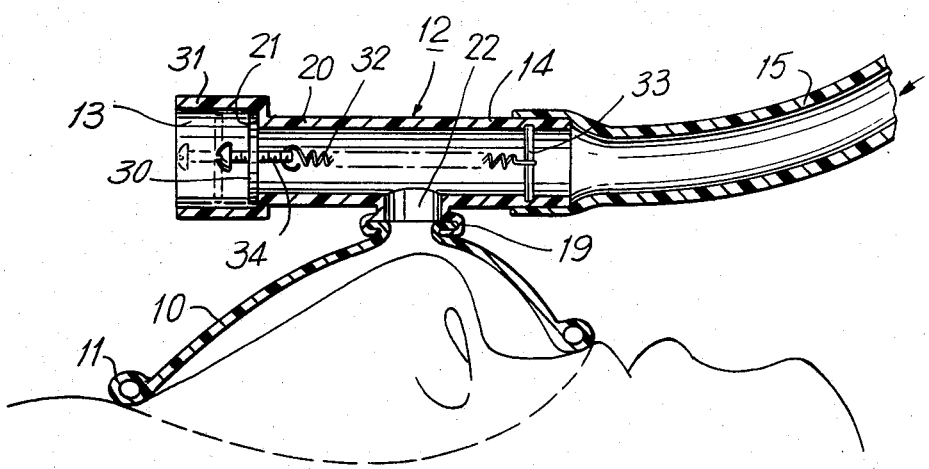
FIG. 2 is a cross-section view of one embodiment of a mask assembly in accordance with the invention.

One embodiment of a nose mask in accordance with the invention is more clearly illustrated in the cross-sectional view of FIG. 2. In this mask, the air cuff seal 11 is of a light plastic material, and must be of a non-irritating material, since it continually contacts the face of the patient. The nose piece 10 is of a plastic material that is partially rigid and partially flexible, such as heavy vinyl, of a nature that can conform with the face. The element must be sufficiently large to accomodate the noses of all patients who may employ the mask. The partial rigidity is required so that the nose piece will generally maintain its shape in use, while still enabling it to conform to the face of the patient.

The nose piece 10 is preferably connected to the valve assembly 12 by way of a swivel joint 19. The valve assembly is comprised of a plastic tube 20, one end of the tube forming a valve seat 21, and the other end 14 being adapted to being interconnected to tube 15 by any conventional means. The side of the tube 20 is provided with an aperture 22 defining the swivel interconnection with the nose piece 10. While any conventional swivel interconnection may be provided, it is desirable in accordance with the invention that the swivel interconnection between the valve assembly and the nose piece 10 be as short as possible, thereby to minimize the size and weight of the nose mask. The swivel interconnection minimizes danger of tangling of the tube during the night, as a result of movement of the patient.

The valve in accordance with the invention may be simply comprised of a rigid valve disk 30 held adjacent the valve seat 21. The disk 30 may be loosely axially guided at its edge by an enlarged diameter end section 31 of the tube 20. The valve disk 30 is urged toward the valve seat 21 by a spring, such as helical spring 32 extending through the tube 20 to a fixed connection, for example, to a pin 33 held to the walls of the tube. Adjustability of the threshold pressure of the valve may be effected by connecting the end of the spring 32 to the end of an adjustment screw 34 threaded in the disk 30. The adjustment of the screw thereby controls the tension of the spring, to determine the pressure within the mask. The mask may be set, for example, to have a threshold from 5 to 15 centimeters $H_2O$. The pressure adjustment for any patient is set so that under normal breathing conditions the valve is always open, even during inhalation. As a result, the required positive pressure is always present to maintain the nasopharyngeal airway opened. As a result of the use of the threshold valve in accordance with the invention, air exhaled by the patient is immediately exhausted by way of the threshold valve, without affecting contamination of the air supplied to the mask. The tube for supplying air to the mask may hence be very small and flexible. The threshold valve itself may be of very simple construction, and is adapted for miniaturization, thereby to minimize the size and weight of the mask.

The internal end of the of cup-shaped element 10, is not critical, aside from being of a size sufficiently large to cover the nose of any patients, since this space is flushed in use by a large flow of air, for example, 40–50 liters per minute. The element preferably has a minimum height, however, in order to minimize the "leverage effect" of forces on the tube 15 dislodging the seal.

The compressed air may be provided by any conventional device, so that the patient may inexpensively provide this source for use at his own home. The compressed air may be heated and humidified by conventional heaters.

In the treatment of obstructive apnea, it must be stressed that the condition can be expected to continue for the remainder of the patients life, and it can be expected to increase in severity. Accordingly, a patient seeking relief by the use of CPAP can expect to require use of the mask for the rest of his life, so that the effectiveness of treatment CPAP depends upon the willingness of the patient to use a nose mask. The nose mask should be employed during naps as well as during nightime sleeping.

The present invention therefore solves the problem of providing the required comfortableness of a nose mask, thereby minimizing the reluctance of patients to seek relief by this means. The mask and method in accordance with the invention may be readily employed in the patients home, and provide an inexpensive solution to the problem.

While the specific threshold valve disclosed above constitutes one embodiment of the invention, it is apparent that the invention is not limited to this disclosed structure. Thus, other valves which enable the release of pressure at a determined thresholds, in order to normally maintain a flow of pressure therethrough, may be employed.

While the invention has been disclosed and described with reference to a single embodiment, it will be apparent that variations and modifications may be made therein, and it is therefore intended in the following claims to cover each such variation and modification as falls within the true spirit and scope of the invention.

What is claimed is:

1. A method of treatment of a patient for obstructive sleep apnea, comprising the steps of applying compressed air continually to a nose mask fitted to cover the patient's nose, maintaining a positive pressure of air within said mask to maintain the nasopharyngeal airway of a patient open, continually exhausting air from said mask by way of a threshold valve which is continually open during normal respiration of the patient, said valve operates in one of a seated state in the absence of said compressed air pressure and in a continuous unseated state when said nose mask is donned on a patient and application of said compressed air pressure to said nose mask causes said valve to operate in said continuously unseated state, said valve being adjustably biasable to select an operating pressure within said mask in a range of from 5 to 15 centimeters of $H_2O$, and further comprising the step of selecting a positive pressure for treatment of said patient within said range by adjusting said bias.

* * * * *